United States Patent [19]

Danner et al.

[11] Patent Number: 4,698,166
[45] Date of Patent: Oct. 6, 1987

[54] METHOD AND APPARATUS FOR PRODUCING A PRODUCT WHICH STIMULATES SKIN RESPIRATION AND PRODUCT PRODUCED THEREBY

[75] Inventors: Michael E. Danner, Kenton Hills, Ky.; Thomas E. Hieber, Cincinnati, Ohio

[73] Assignee: Sperti Drug Products, Inc., Erlanger, Ky.

[21] Appl. No.: 823,226

[22] Filed: Jan. 28, 1986

[51] Int. Cl.⁴ .......................................... B01D 13/00
[52] U.S. Cl. ..................................... 210/774; 203/43; 210/806; 210/808
[58] Field of Search ............... 210/259, 175, 194, 767, 210/768, 294, 772, 773, 295, 774, 790, 314, 805, 806, 808, 181, 182, 322, 323.1, 542; 424/59, 60, 114, 115, 118–123, 167, 177, 180, 181, 195, 343, 358, 359, 364–366; 23/293 R, 297; 203/39, 43–46, 91

[56] References Cited

U.S. PATENT DOCUMENTS 4,072,610 2/1978 Gow et al. .......................... 210/259

Primary Examiner—Frank Sever
Attorney, Agent, or Firm—Kinney & Schenk

[57] ABSTRACT

A method and apparatus for producing a product which stimulates skin respiration and product produced thereby are provided wherein the method comprises the steps of mixing bakers yeast and alcohol in an extractor to produce a slurry of solids and liquid, heating the slurry to a predetermined temperature to produce a heated slurry, holding the heated slurry at the predetermined temperature for a predetermined time, passing the heated slurry through a filter to remove the solids and produce a filtered liquid, placing the filtered liquid in a sterile vacuum still and boiling the filtered liquid in said vacuum still to drive off a substantial percentage of the liquid therein and produce the product, and then further filtering the product in a closed pressure filtering system followed by filtering of the further filtered product through a sterile filter.

20 Claims, 3 Drawing Figures

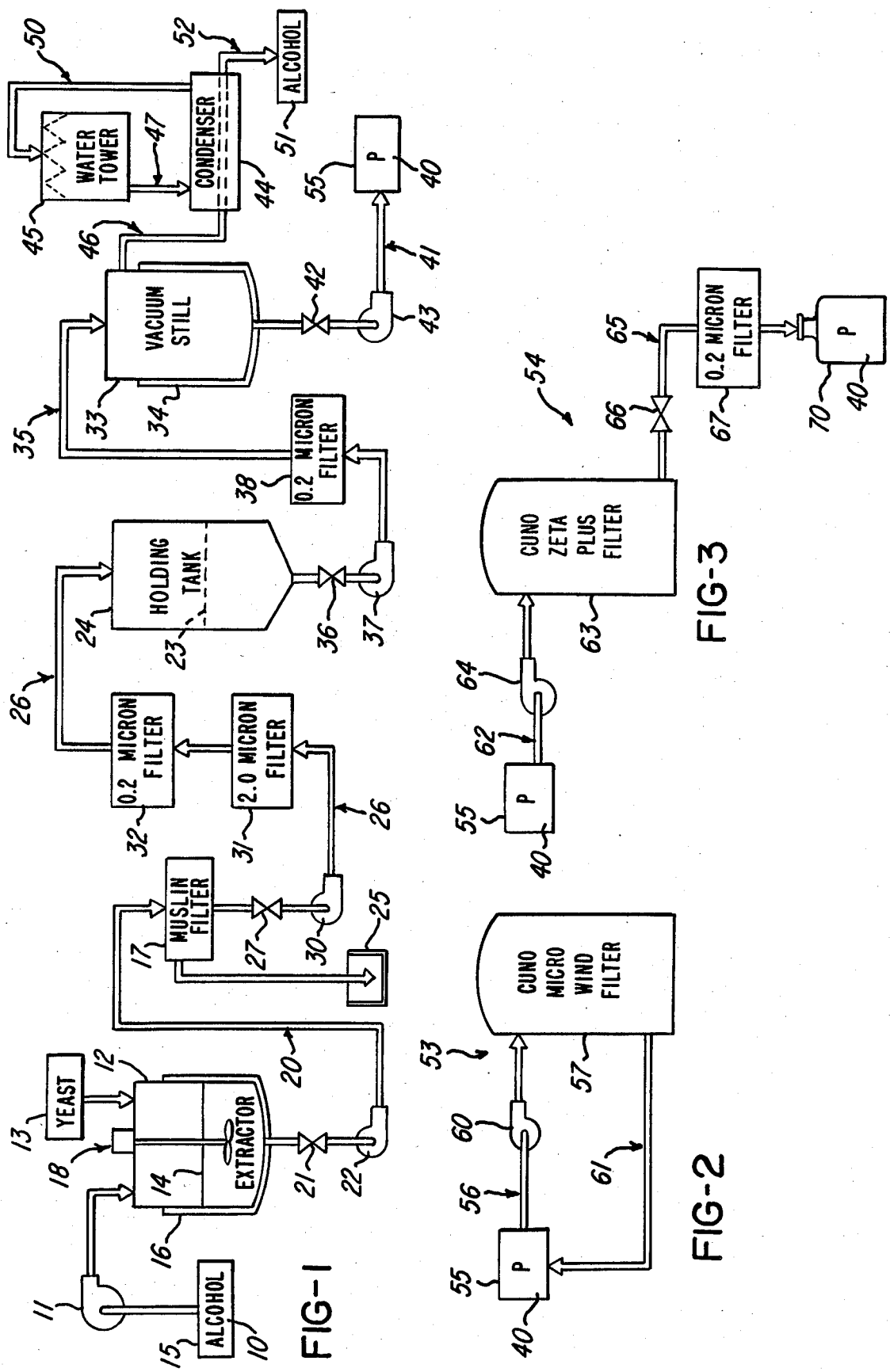

METHOD AND APPARATUS FOR PRODUCING A PRODUCT WHICH STIMULATES SKIN RESPIRATION AND PRODUCT PRODUCED THEREBY

BACKGROUND OF THE INVENTION

1. Field of the Invention

This invention relates to a method and apparatus for producing a product which stimulates skin respiration, or the like, and a product made using such method and apparatus; and, such product may be of the type used in salves, ointments, unguents, cosmetic creams, moisturizing creams, and has particular application in rectal ointments.

2. Prior Art Statement

It is known in the art to provide a method of producing a crude substance which stimulates skin respiration and as disclosed in U.S. Pat. Nos. 2,320,478 and 2,320,479, for example.

It is also known to provide a method and apparatus for producing a product which stimulates skin respiration, or the like, and wherein the method comprises the steps of mixing bakers yeast and alcohol in an extractor to produce a slurry of solids and liquid, heating said slurry to a predetermined temperature to produce a heated slurry, holding said heated slurry at said predetermined temperature for a predetermined time period, passing said heated slurry through a filter to remove said solids and produce a filtered liquid, placing said filtered liquid in a sterile vacuum still, and boiling said filtered liquid in said vacuum still to drive off a substantial percentage of the liquid therein and produce said product.

SUMMARY OF THE INVENTION

One feature of this invention is to provide a new method of producing a product which stimulates skin respiration, or the like, and wherein the method comprises the steps of mixing bakers yeast and alcohol in an extractor to produce a slurry of solids and liquid, heating said slurry to a predetermined temperature to produce a heated slurry, holding said heated slurry at said predetermined temperature for a predetermined time period, passing said heated slurry through a filter to remove said solids and produce a filtered liquid, placing said filtered liquid in a sterile vacuum still, and boiling said filtered liquid in said vacuum still to drive off a substantial percentage of the liquid therein to produce the product and wherein further steps are utilized resulting in said product which is of better quality, provides greater skin respiration, and provides economic advantages.

In accordance with one embodiment of this invention the new method comprises the further steps of further filtering the product in a closed pressure filtering system followed by filtering of the further filtered product through a sterile filter.

In accordance with another embodiment of this invention the new method comprises the further steps of further filtering said filtered liquid through a sterile filter prior to the placing step to thereby remove bacteria which may be present therein.

Accordingly, it is an object of this invention to provide a new method of producing a product which stimulates skin respiration, or the like, with the method of this invention having one or more of the novel features as set forth above or hereinafter described.

Another object of this invention is to provide a new apparatus for producing a product which stimulates skin respiration.

Another object of this invention is to provide a product of the character mentioned made by the new method and apparatus of this invention.

Other features, objects, uses, and advantages of this invention are apparent from a reading of this description which proceeds with reference to the accompanying drawings forming a part thereof.

BRIEF DESCRIPTION OF THE DRAWINGS

The accompanying drawings show present preferred embodiments of this invention, in which FIG. 1 is a primarily schematic view illustrating one exemplary embodiment of the method and apparatus of this invention; and FIGS. 2 and 3 are schematic presentations which are similar to FIG. 1 and show further processing of the product produced by the method and apparatus of FIG. 1.

DESCRIPTION OF THE PREFERRED EMBODIMENTS

While the various features of this invention are hereinafter illustrated and described as being particularly adapted to provide a particular product having certain identified uses, it is to be understood that the various features of this invention can be utilized singly or in various combinations thereof to provide other similar products having other similar uses, as desired. Further, this invention is not to be limited to only the embodiments illustrated in the drawings, because the drawings are merely an example of this invention.

Reference is now made to FIG. 1 of the drawings which illustrates one exemplary embodiment of the new method and apparatus of this invention.

In the method and apparatus of FIG. 1 alcohol in the form of ethyl alcohol 10 is pumped by a pump 11 into a container which will be referred to as an extractor 12; and, in the extractor 12 bakers yeast 13 is mixed therewith to produce a slurry 14 of solids and liquid (alcohol). The ethyl alcohol may be SDA-3A alcohol and the bakers yeast may be of the type commercially available from either Fleischmann or Budweiser, for example. The alcohol 10 is usually pumped from either an associated container 15 which may be a receiving container therefor or a drum (usually of 55 gallon capacity) used to store and transport same. The bakers yeast usually comes in dry form and in 50 lb. bags whereby it is, in essence, dumped into the extractor 12.

The extractor 12 is a stainless steel extractor and has means for heating same and controlling the temperature of its contents and in particular the temperature of the slurry 14 therein and such means is in the form of a hot water jacket 16. The hot water jacket 16 is of conventional construction and therefore will not be described further. The extractor 12 also has a mixer shown in the form of an electric motor driven mixer 18 and the mixer is used to mix thoroughly the bakers yeast and alcohol during the extraction process.

The slurry is heated in the extractor 12 using the hot water jacket 16 to a predetermined temperature to produce a heated slurry and generally such slurry is heated to a predetermined temperature ranging between 60° and 70° C. The heated slurry is held at said temperature ranging between 60° and 70° for a time period generally of the order of four hours. It will be appreciated that extraction may take place at other temperatures and the slurry may be held in the extractor for time periods other than approximately four hours; however, it has been found that the temperatures and time mentioned produce optimum results.

The heated slurry is then passed, i.e. filtered, through a filter shown in this example as a muslin filter 17 and the filtering through such muslin filter is achieved by pumping the heated slurry under pressure through a conduit 20 which is in fluid flow communication with the bottom of the extractor 12 and with the top of the filter 17. The conduit 20 has shutoff valve 21 therein and a pump 22 which is used to pump the heated slurry and pass same through the muslin filter 17.

Any suitable filter may be utilized at this point and the filter 17 is identified as a muslin filter in that it is made of a coarse grade muslin and is used to take out the heavy particulate matter generated by the yeast in the extraction stage. The filter 17 filters out all of the yeast particles in the liquid to produce a filtered liquid 23 which is further filtered as will be described later and then temporarily held or stored in a holding tank 24. The solids from the muslin filter 17 are collected in a receptacle or tank 25 and discarded. The filtered liquid 23 is preferably further filtered employing a pressure pumping system; and, this is achieved by moving the filtered liquid to the holding tank 24 under pressure through a conduit 26 which has a suitable flow control valve 27 and another pump 30 therein. The pump 30 moves the filtered liquid 23 preferably through what may be considered a coarse filter which is shown in the drawings as a 2.0 micron filter 31 and then through much smaller filter 32 preferably of the order of a 0.2 to 0.45 micron filter. The filter 32 removes bacteria and what is considered a spore former which is usually present in the filtered liquid 23.

The holding tank 24 is also a stainless tank and may be used to accumulate filtered liquid prior to further processing. Ordinarily, for one extraction, 1200 lbs. of bakers yeast are utilized with approximately 160 gallons of alcohol and the resulting filtered liquid of the extraction which is moved on to the holding tank 24 is approximately 150 gallons, of liquid. If desired, the holding tank 24 may be used to accumulate several extractions of filtered liquid before further processing.

The filtered liquid 23 in the holding tank (as further filtered by filters 31 and 32) is then placed in a sterile vacuum still 33. The vacuum still 33 is a stainless steel vacuum still of known construction and has a hot water jacket 34 for controlling the temperature thereof.

Prior to placing the filtered liquid 23 which is in the holding tank 24 in the vacuum still 33 the system downstream of such tank 24, including the still 33, is sterilized. Preferably, sterilization of all such downstream system components is achieved by flowing steam under pressure through the conduit 35 connected between the holding tank 24 and the vacuum still 33 and an associated valve 36, pump 37, and filter 38 connected in the conduit 35, as well as the still 33. The steam under pressure is generally steam at a pressure of approximately 15 psig and at a temperature of roughly 200° F.

The filtered (approximately 150 gallons) liquid in tank 24 is then pumped by pump 37 into the sterile vacuum still 33 and the use of sterile components assures minimum bacteria build up. In addition, the filter 38 is preferably a 0.2 micron filter which has been sterilized as described above; and, it will be appreciated that bacteria is eliminated merely by passing filtered liquid 23 through filter 38 of 0.2 micron size.

The filtered liquid 23 in the vacuum still 33 is then boiled to drive off a substantial percentage of the liquid therein and produce the product 40 which is also designated by the letter P and such product is conveyed from the bottom of the vacuum still through a conduit 41, which has a valve 42 and a pump 43 therein, into a suitable container 55. As indicated earlier, approximately 150 gallons of liquid from each batch of material is disposed in the still and after the liquid is driven off approximately 5 to 7 gallons of product 40 results and such product has the rough consistency of ordinary table syrup used for human consumption.

As is known in the art, the vacuum still 33 has a condenser 44, water tower 45, and suitable conduits 46, 47, and 50 therebetween which allows recovery of the alcohol evaporated from the vacuum still in a suitable container 51 by means of a conduit 52 from the condenser 44.

Inasmuch as the operation of the vacuum still 33, condenser 44, water tower 45, are well known in the art, a further more detailed description of these components will not be presented. However, it is to be understood that the water tower 45 with its cool water serves to make the operation of the condenser 44 more efficient.

In accordance with the method of this invention the 5–7 gallons of product 40 is further filtered first as shown in FIG. 2 and then as shown in FIG. 3 as will now be described in detail to thereby provide the final product 40. Indeed, the product 40 after having been processed utilizing the method and apparatus of this invention has been shown to have greater activity level and provide greater skin respiration for any particular quantity of product than was previously possible using methods and apparatus which were known prior to this invention. The net effect of providing a product which provides greater skin respiration is that a lesser amount of such product is required in a particular application and for any given level of required skin respiration whereby the overall cost of the end product is less and hence more competitive.

The product 40, as it exits conduit 41 is placed in container 55, as mentioned earlier, and is then further filtered using a closed pressure filtering system which is designated generally by the reference numeral 53 in FIG. 2 of the drawings followed by further filtering in a single pass pressure filtering system designated generally by the reference numeral 54 and shown in FIG. 3. The systems 53 and 54 will now be described in detail.

In particular, to further filter the product 40 collected from conduit 41 in the closed pressure filtering system 53 such product 40 as disposed in its receptacle 55 (or a similar container, also designated 55) is moved through a conduit 56 to what will be referred to as a microwind filter 57 under positive pressure which is provided by a pressure pump 60 connected in the conduit 56. The product exiting the filter 57 is returned to the tank 55 of FIG. 2 through a conduit 61. The filtering action with the closed pressure filtering system 53 results in passing the product through the microwind filter 57 a plurality of passes which may be as many as 6 passes or more and at this stage of a particular operation approximately 5–7 gallons of product 40 are in the container 55 and being further processed.

To improve the filtering action a material which aids in filtration is introduced into the product 40; and, while any one of several products may be utilized the preferred product is diatomaceous earth which will be referred to hereinafter throughout this specification as simply DE. The DE is added in the amount of approximately 10 grams per liter and inasmuch as roughly 5-7 gallons of product 40 are utilized which is approximately 18 to 20 liters, roughly 150 to 180 grams of DE is utilized and mixed with 5-7 gallons of product 40. The DE builds up a coating on the filter 57 which helps in the filtering action. It will be appreciated that product 40 has a consistency of syrup and it is very difficult to filter same utilizing a very fine filter without some filtering material, or the like, to aid in filtration because the filter tends to "bind off" or clog. The filter 57 filters out gels, bacteria, etc., and the DE serves to give what is commonly referred to in the art as depth to the filter. The filtration in the closed or closed loop filtering system 53 is normally achieved for approximately one hour. However, ordinarily as the number of passes through filter 57 is increased more gels and bacteria are filtered from the product 40.

The conduits 60 and 61 are made utilizing clear materials such as clear plastic, glass, or the like and the filtering action is ordinarily continued until the product 40 has a clear or clean appearance, based on operating experience. Generally, the filtering action is stopped once the pressure in the closed pressure system is around 25 psig and the product 40 is in a clear state as indicated earlier.

During the filtering action in the closed pressure filtering system 53, a cover is maintained on the container 55. It will be appreciated that the filter 57 is of the type which is replaced and not washed when clogged. Depending upon the amount of bacteria and gels still present in the product 40 at this stage it may be necessary that the filter 57 be replaced ever after a single pass therethrough. After filtering through the filter 57 the entire housing of the filter 57 is drained of all product 40 therein and returned into the container 55.

The filter 57 is a 3.0 micron filter and as indicated earlier the filtering action is achieved to remove bacteria, gels, and the like until product 40 is in a clear state. It will be appreciated that the filtering action provided in the closed loop system 53 is such that DE is not inadvertently introduced into the product 40 yet a sufficient amount of DE is added to aid filtration.

After filtering in the closed loop pressure filtering system 53 the actual container 55 is moved to provide further filtration in the single pass filtering system 54, illustrated in FIG. 3, whereupon the container 55 is connected by means of a conduit 62 to another filter 63 and another pump 64 is suitably connected in the conduit 62. The filter 63 is in turn connected by a conduit 65 which has a valve 66 and a 0.2 sterile filter 67 also suitably connected therein upstream of a final container 70 in which the finally filtered product 40 is collected.

As indicated earlier, the material 40 which exits the vacuum still 33 has the consistency or viscosity of table syrup. In order to be able to pass material of this character through an 0.2 sterile filter, such as filter 67, it is necessary to achieve the further filtration. In accordance with this invention the closed loop pressure filtering system 53 and the single pass pressure filtering system 54 illustrated in FIGS. 2 and 3 respectively is used to provide such further filtration. It will be understood by those skilled in the art that it is impossible to "cram" or force the material 40 as it exits the vacuum still through an 0.2 sterile filter without further filtering action of the character provided by systems 53 and 54 upstream of such 0.2 sterile filter.

The pressure filtering action in the system 54 is generally at a pressure of the order of 30 psig; however, such pressure may be as high as 80 psig. Further, the filter 67 is a sterile filter and the conduit 65 with its valve 66 are also suitably sterilized allowing the now fully filtered product 40 exiting conduit 65 to be disposed or collected into the sterile container 70.

The container with its product 40 is then stored in a refrigerator, or the like, to provide a cool environment such that the growth of bacteria is essentially prevented. The container 70 may be shipped at ordinary ambient temperatures, if desired, to a customer who utilizes the product 40. However, such customer generally utilizes a preservative in the product 40 to prevent the buildup of bacteria therein, or the like. End products which use the product 40 as a constituent thereof have a shelf life generally of the order of two years.

The new method and apparatus of this invention employs the 2.0 micron filter 31 and the 0.2 micron filter 32 as well as the 0.2 micron sterile filter 38. It was thought prior to this invention that the processing of the filtered liquid 23 in the vacuum still 33 at high temperature together with the presence of alcohol as used herein destroyed substantially all of the bacteria. However, it was discovered by analysis of the material that a spore former was present therein which survived the hostile environment of the vacuum still. This invention resulted in elimination of the spore former.

The thrust of adding the 2.0 micron filter 31 and the 0.2 micron filter 32 together with the 0.2 micron sterile filter 38 resulted in removal of the spore former before heating in the vacuum still. Thus, the filters 31, 32, and 38 before the vacuum still assured that bacteria would not be formed during the time material was being concentrated. Stated otherwise, the system of FIG. 1 assures the sterility of the material going into the still 33 by taking out the so-called spore formers.

Nevertheless, because there may still be bacteria in the product, such bacteria is eliminated in the filtering systems 53 and 54 illustrated in FIGS. 2 and 3 respectively. It will be appreciated that bacteria may be filtered out of a product, as well as destroyed by temperature. Further, the addition of DE in the closed loop pressure filtering system 53 is not an obvious conclusion in this art because of the fear that DE might add impurities to the product during filtration under pressure.

The method and apparatus of this invention results in the final product 40 which has more activity in that it provides greater skin respiration and is produced at a reduced cost. It will also be appreciated that for pharmaceutical purposes filtration of a product through an 0.2 filter is the amount of filtration which is generally considered to produce a sterile product and meets the United States Federal Drug Administration (FDA) standards. However, in order to be able to filter a particular material through an 0.2 micron filter it is generally necessary to do this in several stages. In the FIG. 1 situation the muslin filter 17 and the 2.0 micron filter 31 are utilized. Similarly, in the systems of FIGS. 2 and 3 the filters 57 and 63 are utilized prior to the sterile filter 67.

In this disclosure of the invention the construction of the extractor 12, holding tank 24, and vacuum still 33 are not described in detail. However, it will be appreciated that such components will have used suitable closures, covers, connections for their conduits or pipes, and the like as is known in the art and as required. It will also be appreciated that although not shown, the vacuum still 33 may also be provided with a suitable motor driven mixer, or the like.

In addition, all vessels, filters, conduits or pipes, valves, pumps and the like meet FDA standards and are acceptable for producing a product 40 which meets FDA standards.

As previously mentioned the filter 17 is a cloth filter and may be made of a coarse grade of muslin, or the like. The 2.0 micron filter 31 may be in the form of a sintered stainless steel porous material and is in essence a recleanable or rewashable filter and is a standard product on the market. One source of supply for the filter 31 is Trinity Company of Cleveland, Ohio.

The 0.2 micron filters 32, 38, and 67 are important filters in that each is used to remove bacteria and spore formers as the case may be. Although various companies make filters of this type, filters 32, 38, and 67 which have been used successfully were made by AMF Cuno Division, Meriden, Conn.

The filter 32 is preferably a Cuno 0.2 micron SG grade while the filter 38 is perferably a Cuno 0.2 micron ST filter. Similarly, the filter 67 is preferably a Cuno 0.2 micron ST filter.

The filters 57 and 63 illustrated in FIGS. 2 and 3 of the drawings are also made by AMF Cuno. The filter 57 is referred to as a Cuno microwind filter; and is also referred to as a gradient filter. The filter 63 is also made by AMF Cuno and is referred to as a Zeta plus filter having a 70S designation. The 70S filter is often referred to as a charged depth filter.

As indicated earlier a typical batch of material consists of roughly 1200 lbs. of yeast and 160 gallons of alcohol and after processing through the method and apparatus of FIG. 1 to the holding tank approximately 150 gallons of liquid remains in the holding tank. After further processing of the 150 gallons, approximately 5-7 gallons result in the vacuum still. The boiling in vacuum still 33 is preferably achieved for a time period of roughly 13 hours while keeping the contents of the still 33 at a temperature of roughly between 50° C. and 60° C. while maintaining a vacuum of about 25 inches of water in the still 33. The still 33 is heated by circulating hot water in the jacket 34. As indicated earlier, after further processing approximately 5 gallons remain and are collected in the container 70.

Certain times and temperatures have been presented in this example for operation of the extractor 12 and vacuum still 33. These are typical and have been used successfully but, it is to be understood that other times and temperatures may also be used. In addition with different times and temperatures in still 33 different vacuums may be used.

Thus, it is seen from the foregoing specification that this invention provides a new method and apparatus for producing a product which stimulates skin respiration, or the like, as well as a new product employing such method and apparatus.

While the forms and methods of this invention now preferred have been illustrated and described as required by the Patent Statute, it is to be understood that other forms and method steps can be utilized and still fall within the scope of the appended claims wherein each claim sets forth what is believed to be known in each claim prior to this invention in the portion of each claim that is disposed before the words "the improvement" and sets forth what is believed to be new in each claim according to this invention in the portion of each claim that is disposed after the words "the improvement" whereby it is believed that each claim sets forth novel, useful, and unobvious invention within the purview of the Patent Statute.

What is claimed is:

1. In a method of producing a product which stimulates skin respiration said method comprising the steps of, mixing bakers yeast and alcohol in an extractor to produce a slurry of solids and liquid, heating said slurry to a predetermined temperature to produce a heated slurry, holding said heated slurry at said predetermined temperature for a predetermined time period, passing said heated slurry through a filter to remove said solids and produce a filtered liquid, placing said filtered liquid in a sterile vacuum still, and boiling said filtered liquid in said vacuum still to drive off a substantial percentage of the liquid therein and produce said product, the improvement in said method comprising the further steps of providing a bacteria/spore forming agent-free product which stimulates skin respiration by further filtering said product in a closed pressure filtering system followed by filtering of said further filtered product through a sterile filter.

2. A method as set forth in claim 1 in which said step of further filtering said product in a closed loop system comprises making a plurality of passes through a filter while employing a material which aids in the further filtering action.

3. A method as set forth in claim 2 employing said material in the form of diatomaceous earth.

4. A method as set forth in claim 3 and comprising the further step of filtering said further filtered product under pressure in a single pass through another filter prior to filtering through said sterile filter.

5. A method as set forth in claim 4 in which said step of filtering through said sterile filter comprises filtering through a 0.2 micron sterile filter into a container which is adapted to be used for storage, refrigeration, and shipment purposes.

6. A method as set forth in claim 5 and comprising the further steps of cooling said container and its contents and keeping same in a refrigerated environment to prevent the buildup of bacteria therein.

7. A method as set forth in claim 5 in which said step of heating said slurry comprises heating said slurry to a temperature ranging between 60° and 70° C.

8. A method as set forth in claim 7 in which said holding step comprises holding said heated slurry at said temperature ranging between 60° and 70° C. for approximately 4 hours.

9. A method as set forth in claim 8 in which said step of boiling said filtered liquid in said vacuum still comprises maintaining said filtered liquid in said vacuum still at a temperature ranging between 50° C. and 60° C. while maintaining a vacuum of 25 inches of water in said still to thereby enable alcohol in said filtered liquid to be driven off at a lower temperature.

10. A method as set forth in claim 9 in which said step of boiling said filtered liquid in said vacuum still comprises boiling said liquid for a time period generally of the order of 13 hours.

11. A method as set forth in claim 9 and comprising the further step of filtering the filtered liquid through a 0.2 micron size sterile filter disposed upstream of said sterile vacuum still before said boiling step.

12. A method as set forth in claim 11 and comprising the further step of filtering through said 0.2 micron sterile filter disposed upstream of said sterile vacuum still after first filtering the liquid through a filter generally of the order of 2.0 microns in size and then through a filter generally of the order of 0.2 micron size.

13. In a method of producing a product which stimulates skin respiration said method comprising the steps of, mixing bakers yeast and alcohol in an extractor to produce a slurry of solids and liquid, heating said slurry to a predetermined temperature to produce a heated slurry, holding said heated slurry at said predetermined temperature for a predetermined time period, passing said heated slurry through a filter to remove said solids and produce a filtered liquid, placing said filtered liquid in a sterile vacuum still, and boiling said filtered liquid in said vacuum still to drive off a substantial percentage of the liquid therein and produce said product, the improvement in said method comprising the further steps of providing a bacteria/spore forming agent-free product which stimulates skin respiration by further filtering said filtered liquid through a sterile filter prior to said placing step to thereby remove bacteria which may be present therein.

14. A method as set forth in claim 13 in which said step of further filtering said filtered liquid through a sterile filter comprises filtering said filtered liquid through a sterile filter generally of the order of 0.2 micron size.

15. A method as set forth in claim 14 and comprising the further step of filtering said filtered liquid first through a filter generally of the order of 2.0 microns in size and then through a filter generally of the order of 0.2 micron size prior to filtering through said sterile filter of 0.2 micron size.

16. A method as set forth in claim 15 in which said heating step comprises heating said slurry to a temperature ranging between 60° C. and 70° C.

17. A method as set forth in claim 16 in which said holding step comprises holding said heated slurry at said temperature ranging between 60° and 70° C. for approximately 4 hours.

18. A method as set forth in claim 17 in which said step of boiling said filtered liquid in said vacuum still comprises maintaining said filtered liquid in said vacuum still at a temperature ranging between 50° C. and 60° C. while maintaining a vacuum of 25 inches of water in said still to thereby enable alcohol in said filtered liquid to be driven off at a lower temperature.

19. A method as set forth in claim 18 in which said step of boiling said filtered liquid in said vacuum still comprises boiling said liquid for a time period generally of the order of 13 hours.

20. A method as set forth in claim 19 in which said step of filtering through said sterile filter of 0.2 micron size comprises filtering therethrough and into a container which is adapted to be used for storage, refrigeration, and shipment purposes.

* * * * *